US00PP10978P

United States Patent [19]

Larsen et al.

[11] Patent Number: Plant 10,978

[45] Date of Patent: Jun. 29, 1999

[54] OSTEOSPERMUM PLANT NAMED 'SUNNY MARTHA'

[75] Inventors: Bjarne Larsen; Niels Larsen, both of Odense N, Denmark

[73] Assignee: Paul Ecke Ranch, Encinitas, Calif.

[21] Appl. No.: 08/959,899

[22] Filed: Oct. 29, 1997

[51] Int. Cl.[6] ..... A01H 5/00

[52] U.S. Cl. ..... Plt./360

[58] Field of Search ..... Plt./65.1, 360

*Primary Examiner*—Howard J. Locker

*Assistant Examiner*—Melissa L. Kimball

*Attorney, Agent, or Firm*—C. A. Whealy

[57] ABSTRACT

A distinct cultivar of Osteospermum plant named 'Sunny Martha', characterized by its upright growth habit with dense foliage and erect flower stems; rapid growth rate; light lavender ray florets with violet blue disc florets; and numerous inflorescences per plant.

1 Drawing Sheet

The present invention relates to a new and distinct cultivar of Osteospermum plant, botanically known as *Osteospermum ecklonis* and referred to by the cultivar name. The new Osteospermum was tested under the name 2.98.96.

The new cultivar is a product of a planned breeding program conducted by the inventors in Odense, Denmark. The objective of the breeding program was to create new Osteospermum cultivars having uniform plant habit and interesting floret colors and leaf shape.

The new cultivar originated from a self-pollination made by the inventors of the *Osteospermum ecklonis* proprietary selection identified as code number 2.54.93. The new Osteospermum was selected by the inventors from the progeny of this cross in a controlled environment in Odense, Denmark, in 1995. Plants of the new Osteospermum differ from plants of the parent selection in floret color and inflorescence size.

Asexual reproduction of the new cultivar by terminal cuttings taken at Odense, Denmark, has shown that the unique features of this new Osteospermum are stable and reproduced true to type in successive generations.

The following traits have been repeatedly observed and are determined to be the unique characteristics of 'Sunny Martha'. These characteristics in combination distinguish 'Sunny Martha' as a new and distinct cultivar:

1. Upright growth habit with dense foliage and erect flower stems.
2. Rapid growth rate.
3. Light lavender ray florets with violet blue disc florets.
4. Numerous inflorescences per plant. Plants flower continuously.

The cultivar Sunny Martha has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Sunny Martha'.

The photograph at the bottom of the sheet is a close-up view of typical inflorescences (upper surface, left, and under surface), right) and leaves (center) of 'Sunny Martha'. Foliage and floret colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown outdoors in containers during the spring in Encinitas, Calif. and Keller, Tex. Measurements and numerical values represent averages for typical flowering plants.

Botanical classification: *Osteospermum ecklonis* cultivar Sunny Martha.

Parentage: Self-pollination of the proptrietary selection of *Osteospermum ecklonis,* code number 2.54.93.

Propagation:

*Type*.—Terminal tip cuttings.

*Time to initiate roots*.—Summer: About 11 days at 20° C. Winter: About 15 days at 20° C.

*Time to develop roots* (*time required to produce a rooted cutting*).—Summer: About 18 days at 20° C. Winter: About 25 days at 20° C.

*Rooting habit*.—Fine, fibrous and somewhat branched.

Plant description:

*Appearance*.—Perennial herbaceous container and garden plant. Upright growth habit. Dense foliage and erect flower stems. Freely branching nd growth rate is rapid.

*Plant height*.—About 40 cm.

*Plant spread*.—About 50 cm.

*Foliage description*.—Leaves alternate, single. Length, fully expanded leaves: About 10 cm. Width, fully expanded leaves: About 3.5 cm. Shape: Oblanceolate. Apex: Cuspidate. Base: Attenuate, leaves sessile. Margin: Widely-spaced teeth, 2 to 4 per edge. Aspect: Flat. Texture: Very fine pubescence on both surfaces and at margins. Fragrance: Strongly fragrant, typical of species. Color: Young foliage, upper surface: 146A. Young foliage, under surface: Slightly lighter than 146A. Fully expanded foliage, upper surface: 147A. Fully expanded foliage, under surface: Greener than 146A. Attenuated leaf base: 146D. Venation, upper surface: 146B. Venation, under surface: 146C.

Inflorescence description:

*Appearance*.—Daisy-type composite inflorescence form. Inflorescences borne on terminals above foliage, arising from leaf axils. Disc and ray florets arranged acropetally on a capitulum. One inflorescence per flowering stem. Inflorescences persistent.

*Flowering response*.—Under natural conditions, plants flower continuously from April to October in the Northern Hemisphere.

*Fragrance*.—Slight, typical of species.

*Inflorescence size*.—Diameter: About 7 cm. Depth (height): About 2.5 cm. Diameter of disc: About 1.2 cm.

*Opening inflorescences*.—Length: About 1.3 cm. Width: About 1 cm. Shape: Pointed. Color: 144A.

*Ray florets*.—Length: About 3.3 cm. Width: About 1 cm. Shape: Oblanceolate. Apex: Rounded or somtimes retuse. Margin: Entire. Texture: Satiny, smooth. Number of ray florets per inflorescence: About 20. Color: When opening: 75A. Mature, upper surface: 75C/75D, color fades to white with subsequent development. Mature, under surface: 75C/75D with dark purple center stripe, 83B.

*Disc florets*.—Length: About 7.5 mm. Width: About 1 mm at base, flaring to about 2 at apex. Shape: Tubular, slightly funnel-shaped. Number of disc florets per inflorescence: Numerous. Color: Immature: 96A. Mature: 94A.

*Peduncle*.—Length: About 12 cm. Diameter: About 2 mm. Aspect: Strong, inflorescences held erect above foliage. Texture: Rough, slightly pubescent. Color: 144A.

*Sepals*.—Appressed to ray florets. Shape: Narrowly lanceolate with pointed apex. Quantity: About 20 per inflorescence. Texture: Rough with short coarse hairs. Color: 144A.

*Reproductive organs*.—Androecium: Present on disc florets only. Anthers: One per disc floret, 5-parted. Pollen: Golden yellow, moderate. Gynoecium: Present on ray and disc florets. Stigma: Bipartite. Style: Purple. Ovary: Interior, green in color.

Disease resistance: No known Osteospermum diseases observed to date on plants grown under commercial production.

Seed production: Seed production has not been observed.

It is claimed:

1. A new and distinct cultivar of Osteospermum plant named 'Sunny Martha', as illustrated and described.

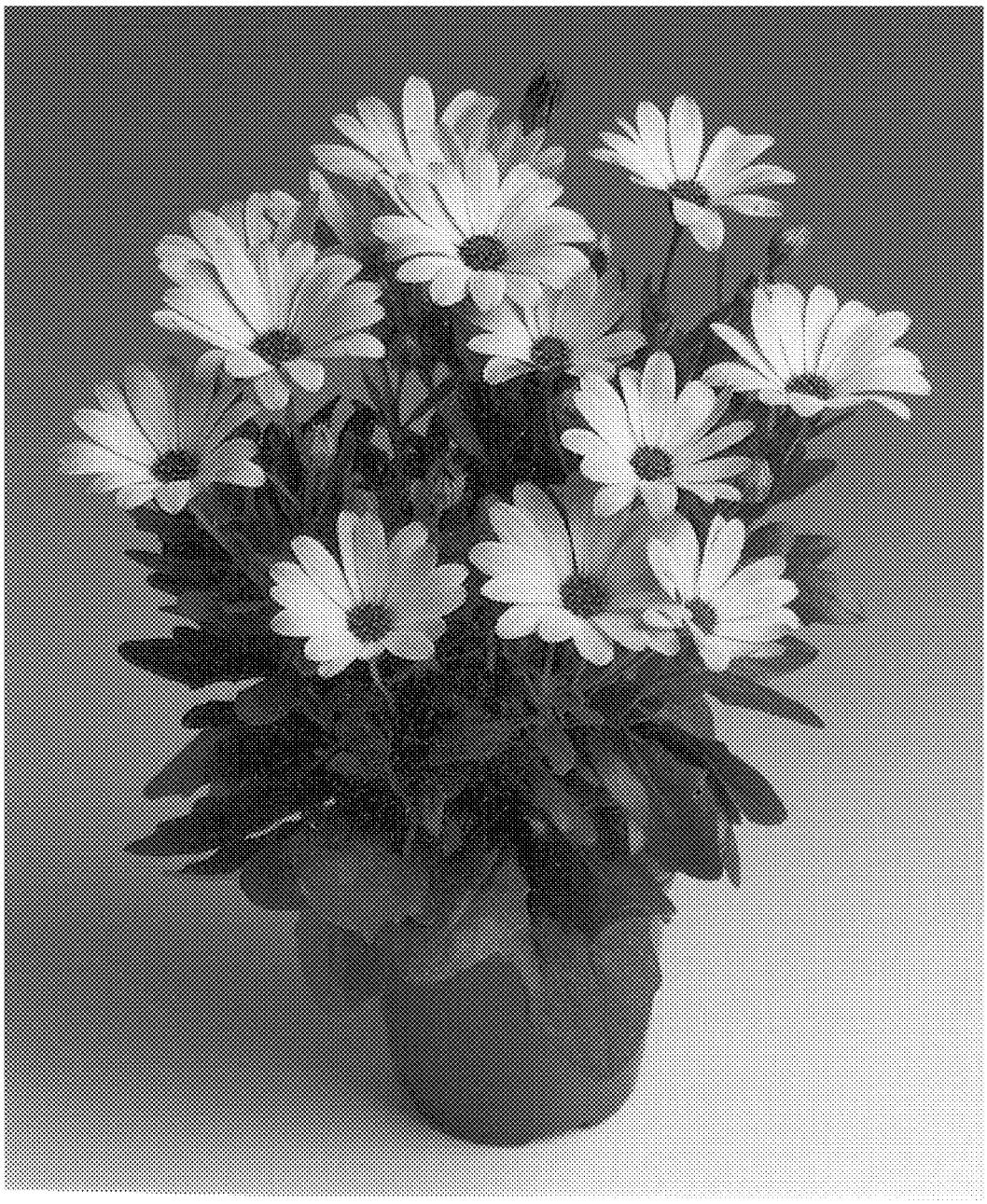
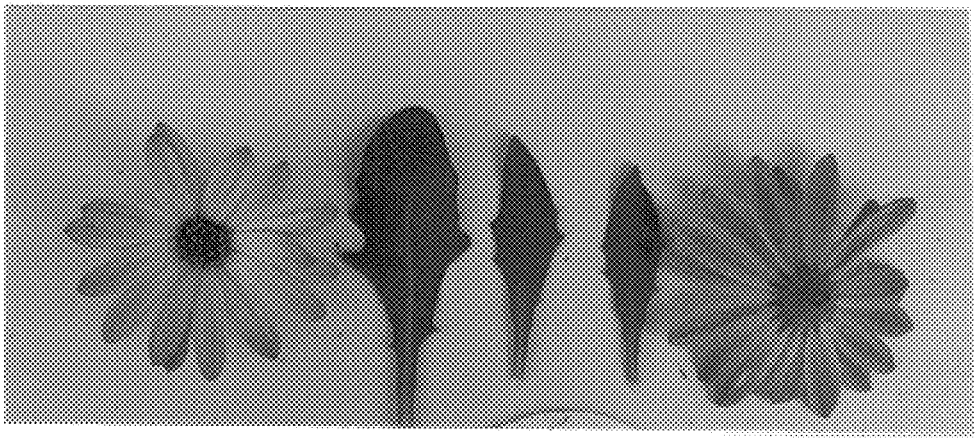

* * * * *